US011207094B2

(12) United States Patent
Banko

(10) Patent No.: US 11,207,094 B2
(45) Date of Patent: Dec. 28, 2021

(54) SINGLE PIECE CONNECTING MEMBER AND WORK TIP FOR SURGICAL HAND PIECE

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 0 days.

(21) Appl. No.: 15/821,137

(22) Filed: Nov. 22, 2017

(65) Prior Publication Data

US 2019/0117253 A1   Apr. 25, 2019

(51) Int. Cl.
*A61B 17/32* (2006.01)
*A61F 9/007* (2006.01)
*A61B 17/00* (2006.01)

(52) U.S. Cl.
CPC .. *A61B 17/320068* (2013.01); *A61F 9/00745* (2013.01); *A61B 2017/0023* (2013.01);
(Continued)

(58) Field of Classification Search
CPC .... A61B 17/320068; A61B 2017/0023; A61B 2017/320075; A61B 2017/0046; A61B 2017/320069; A61B 2017/32007; A61B 2017/320071; A61B 2017/320072; A61B 2017/320073; A61B 2017/320074; A61B 2017/320077; A61B 2017/320078; A61B 2017/32008; A61B 2017/320082; A61B 2017/320084; A61B 2017/320088; A61B 2017/320089; A61B 2017/32009; A61B 2017/320093; A61B 2017/320094; A61B 2017/320095; A61B 2017/320097; A61B 2017/320098; A61B 17/320092; A61B 17/3201; A61F 9/00745; A61N 7/00
See application file for complete search history.

(56) References Cited

U.S. PATENT DOCUMENTS 3,589,363 A   6/1971   Banko et al.
3,906,954 A   9/1975   Baehr et al.
(Continued)

FOREIGN PATENT DOCUMENTS

CN   106175848 A   6/2016
EP   2521509 B1   1/2011

OTHER PUBLICATIONS

International Search Report and Written Opinion in corresponding PCT Application No. PCT/2018/061940, dated Feb. 26, 2019.
(Continued)

*Primary Examiner* — Tan-Uyen T Ho
*Assistant Examiner* — Chima U Igboko
(74) *Attorney, Agent, or Firm* — Leason Ellis LLP

(57) ABSTRACT

A surgical hand piece has a source of ultrasonic energy connected to a one-piece member that transmits the ultrasonic energy. The one-piece member is connected directly to the source of ultrasonic energy without intervening structure. A distal end of the member is a surgical work tip for performing surgery. The member transmits the ultrasonic energy to the work tip. The member is a one-piece structure, whereby the handpiece is less expensive to make than members with multiple piece structures.

3 Claims, 6 Drawing Sheets

(52) U.S. Cl.
CPC ............... *A61B 2017/0046* (2013.01); *A61B 2017/32007* (2017.08); *A61B 2017/320075* (2017.08); *A61B 2017/320084* (2013.01)

(56) References Cited

U.S. PATENT DOCUMENTS

| | | | |
|---|---|---|---|
| 3,976,077 A | | 8/1976 | Kerfoot, Jr. |
| 3,990,452 A | | 11/1976 | Murry et al. |
| 4,168,447 A | | 9/1979 | Bussiere et al. |
| 4,320,761 A | | 3/1982 | Haddad |
| 4,504,264 A | * | 3/1985 | Kelman .............. A61F 9/00745 604/22 |
| 6,214,017 B1 | | 4/2001 | Stoddard et al. |
| 6,443,969 B1 | * | 9/2002 | Novak ........... A61B 17/320068 606/169 |
| 7,083,589 B2 | | 8/2006 | Banko et al. |
| 8,348,967 B2 | | 1/2013 | Stolen |
| 8,641,658 B1 | | 2/2014 | Banko |
| 2002/0007200 A1 | * | 1/2002 | Desinger ........ A61B 17/320068 607/96 |
| 2003/0114873 A1 | * | 6/2003 | Banko ................ A61F 9/00745 606/169 |
| 2003/0212332 A1 | | 11/2003 | Fenton et al. |
| 2005/0020966 A1 | * | 1/2005 | Soring ........... A61B 17/320068 604/22 |
| 2007/0060926 A1 | | 3/2007 | Escaf |
| 2008/0234710 A1 | | 9/2008 | Neurohr et al. |
| 2009/0082716 A1 | | 3/2009 | Akahosi |
| 2014/0276364 A1 | | 9/2014 | Sussman |
| 2014/0029269 A1 | | 11/2014 | Adey et al. |
| 2015/0025451 A1 | * | 1/2015 | Banko ................ A61F 9/00745 604/35 |
| 2016/0374707 A1 | * | 12/2016 | Akagane ............ A61B 18/1402 606/169 |
| 2019/0133823 A1 | | 5/2019 | Banko |

OTHER PUBLICATIONS

International Search Report and Written Opinion in corresponding PCT Application No. PCT/US2019/035747, dated Nov. 25, 2019.
International Preliminary Report on Patentability in corresponding PCT Application No. PCT/US2019/035747, dated Dec. 8, 2020.
International Preliminary Report on Patentability in corresponding PCT Application No. PCT/US2018/061940, dated Jun. 4, 2020.

* cited by examiner

SINGLE PIECE CONNECTING MEMBER AND WORK TIP FOR SURGICAL HAND PIECE

TECHNICAL FIELD

The present invention is generally directed to hand pieces for surgery and particularly for the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

FIG. 1 shows a prior art handpiece as disclosed in U.S. Application Publication 2015/0025451 A1, which was published on Jan. 22, 2015, and names Dr. William Banko as its inventor, i.e., the inventor of the present invention. This hand piece receives electrical energy through wires 40, 41, which drive transducer 11 to create electro-mechanical vibrations. This transducer is in section $M_1$ of the device and it can be either the electromagnetic type or the piezoelectric crystal type. Connected to the transducer 11 is a connecting body 16 in section $M_2$. Both the transducer 11 and connecting body 16 are provided in a housing 10. Although not shown for the sake of clarity, the transducer and connecting body are suspended within housing 10 so as to permit the longitudinal vibration of the transducer and connecting body to occur relative to the housing.

A work tip 14 in section $M_3$ of the handpiece has an opening that leads to an axial channel 25 extending from the opening to an enlarged hub 140 at the proximal end of the work tip. Within the hub 140 there is a radial channel 142 that extends from the axial channel to the outer surface of the hub. A threaded connector 15 extends from the proximal end of the hub and engages the distal end of the connecting body 16.

A sleeve 17, which may advantageously made of silicone, is provided with a funnel shape so that its proximal end is large enough to encompass the enlarged hub, and still leave space for chamber 117 between the outer surface of the hub and the inner surface of the sleeve. The distal end of the sleeve tapers down around the portion 144 of the work tip beyond the hub, which extends to a flared portion 146 of the work tip which is at the operating end. As a result the axial channel has a larger diameter at the operating end that tapers down to a smaller diameter as it extends through the work tip into the hub 140. The sleeve stops short of the portion 146. The proximal end 18 of sleeve 17 makes a threaded connection with the housing 10.

Sleeve 17 has a first external connector 22 on its outer surface that is in fluid communication with the chamber 117. A tube 210 carrying irrigation fluid may be connected to connector 22 in order to supply irrigation fluid to chamber 117. Fluid in chamber 117 may flow between the outer surface of work tip portion 144 and the inner surface of sleeve 17 in a channel 21 so as to exit the handpiece just short of the flared portion 146 of the work tip, i.e., at the site of the operation of the handpiece on the patient's tissue. Sleeve 17 also has a second external connector 24 on its outer surface. A seal piece 148, e.g., an O-ring or other form of seal, connects the radial channel 142 to the second connector 24. A tube 220 provides a suction force (e.g., from a peristaltic aspiration pump) on connector 24. This causes tissue to be drawn into the opening at portion 146 of the work tip, to travel up the axial channel 25 and into the radial channel 142, to pass through the O-ring 148 and the connector 24, and finally to be drawn through tube 220 to the aspiration pump.

In operation the mechanical axial force from transducer 11 is transmitted to the connecting body 16, which in turn transmits it to the work tip 14. When the end 146 of the work tip is placed in contact with tissue, e.g., a cataract, the vibration causes the tissue to break up. While this is occurring, irrigation fluid, e.g., saline solution, passes from a source, through tube 210 and connector 22 into chamber 117, along channel 21 and is deposited at the operating site as shown by the arrows. At the same time the fragmented tissue is drawn into the opening in portion 146 as shown by the other arrow. It passes up the axial channel 25 into the radial channel 142, through the O-ring 148 and connector 24 to tube 220.

The ultrasonic mechanical vibration generates stresses in the handpiece. FIG. 2 shows the sections of the handpiece, i.e., the transducer, the connecting piece $M_1$ and $M_2$, and the work tip $M_3$. Also, FIG. 2 shows the amplitude of the vibrations and the stress in various parts of the hand piece. It can be seen from FIG. 2 that the maximum stress is at the connection between the connecting piece $M_2$ and the work tip $M_3$, which connection is provided by thread 15 (FIG. 1). Unless the threads 15 are machined perfectly and match to a very high tolerance, the transmission of energy will be reduced and dampened in the threaded area between the connecting body and the work tip.

In addition, the typical material used for the connecting piece and work tip is titanium or a titanium alloy. Machining threads into this material is time consuming and difficult, and hence costly. These are a couple of the reasons why the handpiece is relatively expensive.

SUMMARY OF THE INVENTION

In accordance with the invention a surgical hand piece is provided with a solid ultrasonic knife (e.g., scalpel) or hollow tube made of titanium alloy or a material that is less expensive and easier to manufacture than titanium. Further, the threaded connection between the connecting piece and the work tip present in prior designs is eliminated and a single piece is provided for that structure.

Eliminating the threaded connection between the connecting body and the work tip, resulting in one single machined part, will reduce costs tremendously. As noted, cutting threads in the titanium connecting body and the titanium work tip is an expensive and time consuming operation in that it must be done on special machines and takes a long time. A secondary benefit is that the transmission of vibration energy is much more efficient. Thus with increased efficiency less ultrasonic energy needs to be generated in order to have the same output power. This allows for the use of fewer crystals or smaller crystals in a crystal transducer or fewer coils and fewer nickel laminations in a magnetostrictive transducer. This provides another significant saving in manufacturing costs that can result in a disposable ultrasonic handpiece.

In an illustrative embodiment the surgical hand piece has either a hollow tube or a solid blade or knife work tip connected to a source of ultrasonic energy as a one-piece structure. At least one sleeve is provided to provide irrigation or aspiration fluid to the work tip.

BRIEF DESCRIPTION OF THE DRAWINGS

The foregoing and other objects and advantages of the present invention will become more apparent when considered in connection with the following detailed description and appended drawings in which like designations denote like elements in the various views, and wherein.

DETAILED DESCRIPTION OF THE INVENTION

Figure 1:
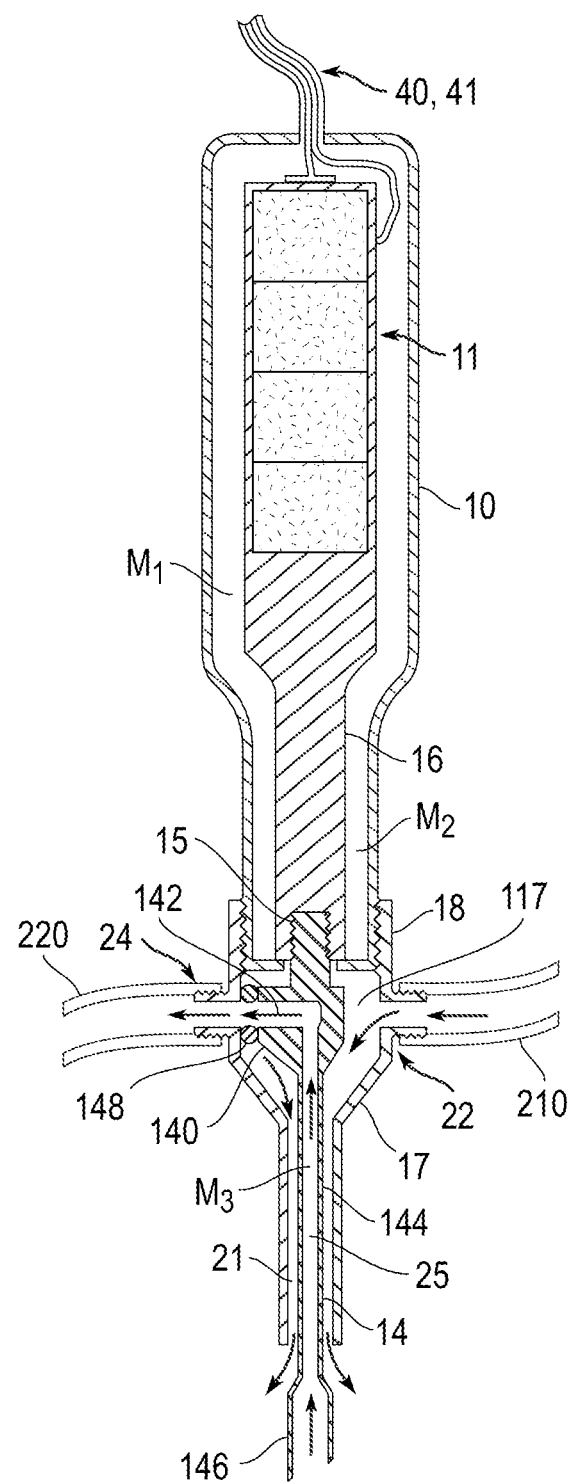
FIG. 1 is a cross section of a prior art surgical handpiece.
Figure 2:
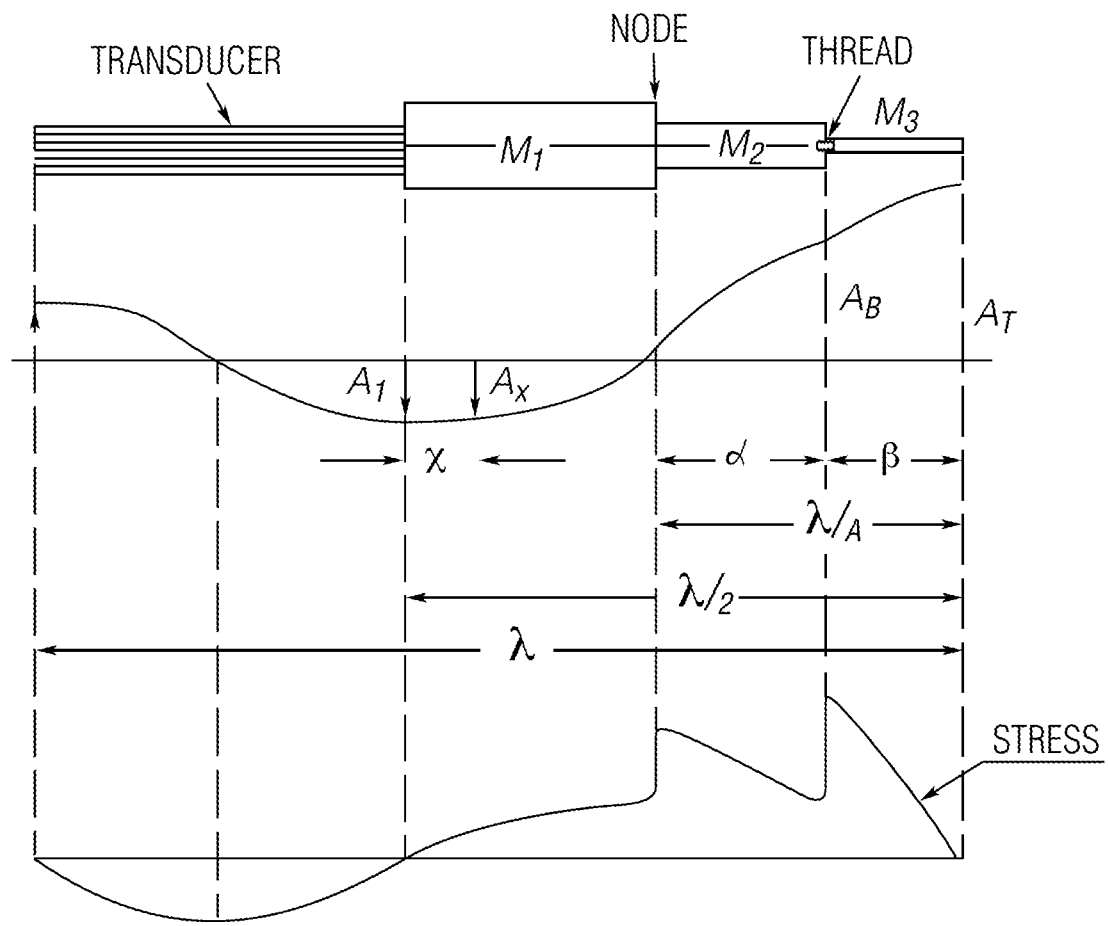
FIG. 2 is a graph showing the amplitude of vibration and the stress for a prior art surgical handpiece like that in FIG. 2.
Figure 3:
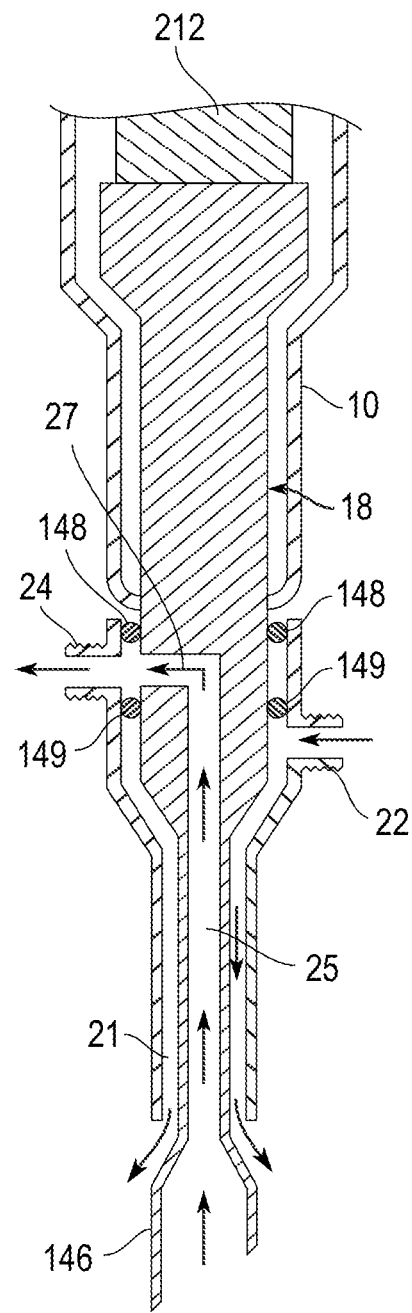
FIG. 3 is a cross section of a surgical hand piece according to the present invention with a hollow tube work tip.

FIG. 3 shows an embodiment of a handpiece according to an illustrative embodiment of the present invention. As with the prior art shown in FIG. 1, this hand piece has an ultrasonic vibration part 212 connected to a work tip 146 by a one-piece member 18, that does not have any threaded connection like thread 15 in FIG. 1. From the work tip 146 there is a channel 25 in the structure that runs axially and then radially in channel 27 to an attachment nozzle 24 in housing 10 for an aspiration line (not shown). An attachment nozzle 22 is provided in the housing 10 for an irrigation line (not shown). Irrigation fluid introduced into nozzle 22 travels in a channel 21 that surrounds the hollow work tip 146 and exits adjacent to the distal end of the work tip. The one-piece member 18 vibrates with respect to the housing 10. O-ring 148 absorbs the vibration and keeps aspiration fluid from leaking into the space between member 18 and the housing proximal of the nozzle 24. An O-ring 149 keeps the aspiration fluid from leaking into the space between the member and housing distal of the nozzle 24. Further, O-ring 149 also keeps irrigation fluid from leaking between the one-piece member and the housing proximal of the nozzle 22, and forms the proximal end of channel 21.

The member 18 with the work tip 146 may be cast as a single piece from titanium or a titanium alloy. Because it has no fine threaded parts, machining may be eliminated or at least reduced. In addition, a single member 18 is more efficient than the separate connecting member 16 and work tip 146 attached by threads 15 as shown in the prior art of FIG. 1. A one piece structure has a lower impedance than two pieces so it requires less energy. In particular, a structure with a low impedance will require less voltage to generate the same amplitude of vibration.

Figure 4:
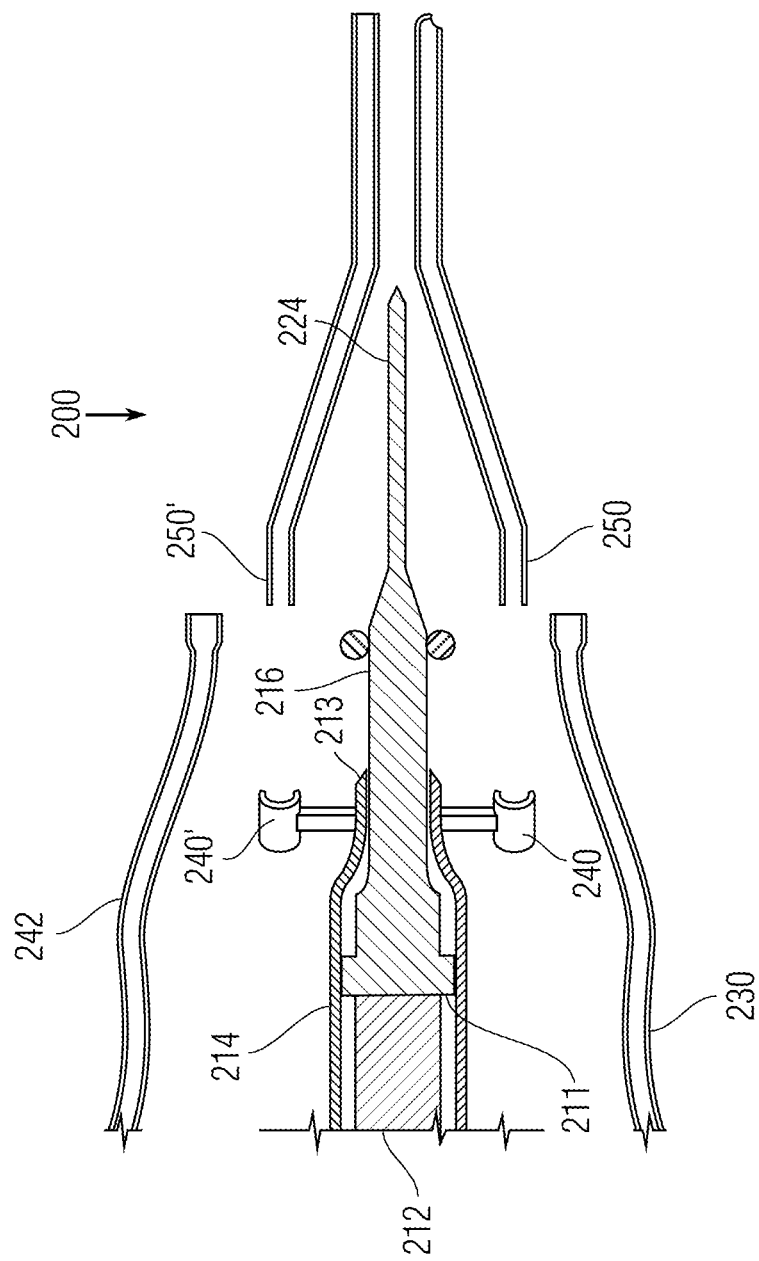
FIG. 4 is an exploded view of a surgical handpiece according to the present invention with a first solid knife work tip embodiment.

FIG. 4 is an exploded view of an alternative embodiment in which the hollow tube work tip 146 of the embodiment of FIG. 3 is replaced with a knife or blade work tip 224. In this embodiment the hand piece 200 has a housing 214. A transducer 212 is provided in the proximal end of the housing for generating ultrasonic linear mechanical vibrations upon excitation with an alternating-current electrical signal. The transducer is supported within the housing 214 by flanges 211. A metal one-piece member 216 has a proximal end portion attached to the transducer 212. The member 216 forms an acoustic impedance transformer for conveying the longitudinal vibrations of the transducer 212 for application to the operative working tip 224, which is in the form of a solid knife or scalpel. The work tip 224 is part of the member 216 and no connecting thread is used.

As null point 213 of the vibration of member 216 is attached to the housing 214. At the same location tube holders 240,240' are attached. An irrigation line 242 is connected to a rigid plastic irrigation line 250'. When assembled as shown FIG. 5 the line 250' is captured in tube holder 240'. Similarly an aspiration line 230 is connected to a rigid plastic aspiration line 250. A sleeve 227 surrounds the knife 224 and its proximal end is blocked by O-ring 223 to keep ocular fluid from flowing back along the knife when the work tip is inserted into the patient's eye during cataract surgery. The sleeve supports the rigid tubes 250, 250' and keeps them in place during use.

Figure 5:
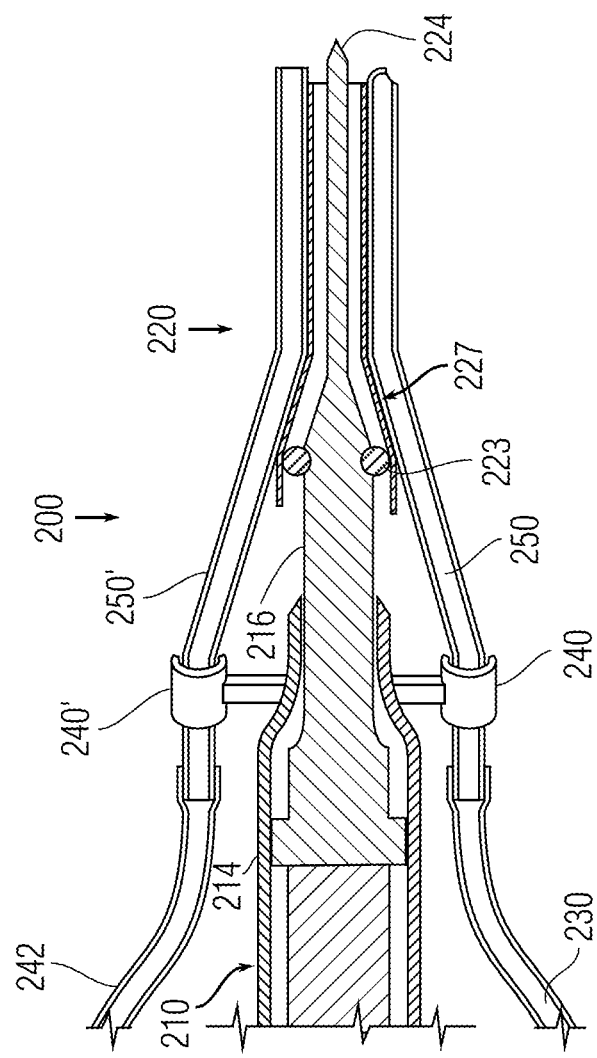
FIG. 5 is a cross section of the fully assembled surgical handpiece of FIG. 4.
Figure 6:
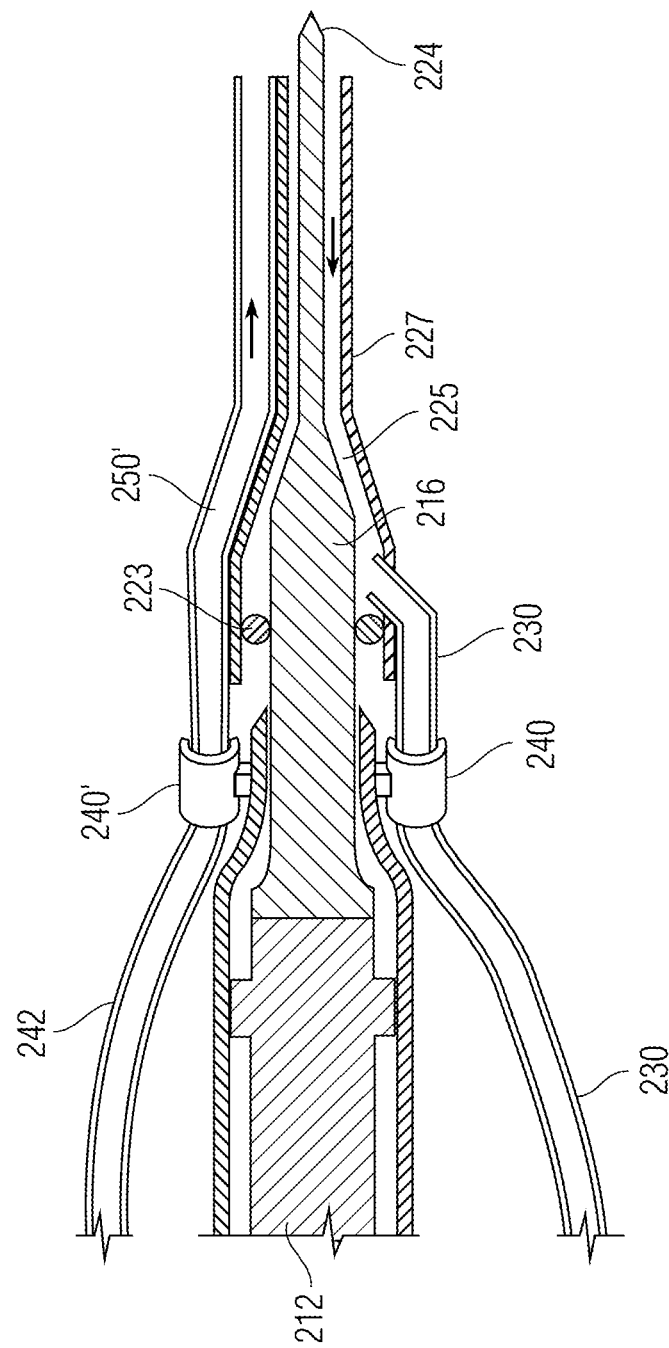
FIG. 6 is a cross sectional fully assembled view of a surgical hand piece according to the present invention with a second solid knife work tip embodiment.

The embodiment of FIG. 6 is similar to that of FIG. 5 in that a one-piece member 216 is connected to the vibration source 212 and extends to solid knife 224 as one structure without a connecting threaded part. The difference between FIG. 5 and FIG. 6 is that the rigid plastic aspiration tube 250 is replaced with a channel 225 that surrounds the knife 224. In particular, the distal end of the line 230 after the tube holder 240 attaches to and penetrates the sleeve 227. O-rings 223 form the proximal end of the channel 225 which extends to the region of the blade 224 to collect emulsified tissue during phacoemulsification.

One of the important features of the embodiments of FIGS. 5 and 6 is that the one-piece member 216 is made of solid material, as opposed to the elongated, hollow titanium alloy tube of FIG. 3. Thus there is no need to machine or drill into the metal to form the channels 25, 27. This reduces the time and complexity of the formation of this part, and thus the cost of manufacturing it.

With the cost savings from eliminating the threaded connection and perhaps the additional savings from eliminating the need to form channels in the metal with the hollow tube work tip, the cost of the hand piece can be sufficiently low that it can be a disposable single-use item. Making the handpiece disposable means there is no longer a need to sterilize the handpiece after use. The sterilization process typically involves moisture and high temperatures. As a result, the handpiece, particularly the ultrasonic transducer, must be made to withstand sterilization, e.g., making the coils of gold wire. Thus, by avoiding sterilization the transducer can be made of less extensive parts (e.g., copper wire) making it even more feasible to have it as a single-use disposable item.

While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A surgical handpiece comprising:
   a source of ultrasonic energy;
   a housing;
   a member connected directly to the source of ultrasonic energy without intervening structure and being within the housing, a distal end of the member is a work tip for performing surgery and which can be vibrated by the ultrasonic energy, said member transmitting the ultrasonic energy to the work tip at a distal end of the work tip; and the housing containing and supporting the source of ultrasonic energy and supporting a proximal portion of the member at a null point in the vibration of the member;

an irrigation line located at least in part adjacent to the member for delivering irrigation fluid to the vicinity of the distal end of the work tip; and an aspiration line located at least in part adjacent the member for drawing tissue and fluid from the vicinity of the distal end of the work tip, wherein said irrigation line and said aspiration line are supported by and located entirely outside of the housing; and wherein the member is a one-piece structure, and wherein the work tip is a solid knife in the form of a scalpel with a sharp edge at its distal end.

2. The surgical handpiece of claim 1 wherein the member is made of titanium or a titanium alloy.

3. The surgical handpiece of claim 1 wherein the handpiece is a single-use disposable item based on the one-piece structure of the member.

* * * * *